US011278639B2

(12) United States Patent
Young et al.

(10) Patent No.: US 11,278,639 B2
(45) Date of Patent: Mar. 22, 2022

(54) HYDROGEL COMPOSITIONS BONDED TO POLYMERIC SUBSTRATES

(71) Applicant: 3M INNOVATIVE PROPERTIES COMPANY, St. Paul, MN (US)

(72) Inventors: Alexi J. Young, Shoreview, MN (US); Jerald K. Rasmussen, Woodville, WI (US)

(73) Assignee: 3M Innovative Properties Company, St. Paul, MN (US)

(*) Notice: Subject to any disclaimer, the term of this patent is extended or adjusted under 35 U.S.C. 154(b) by 260 days.

(21) Appl. No.: 16/485,580

(22) PCT Filed: Mar. 23, 2018

(86) PCT No.: PCT/US2018/023914
§ 371 (c)(1),
(2) Date: Aug. 13, 2019

(87) PCT Pub. No.: WO2018/183098
PCT Pub. Date: Oct. 4, 2018

(65) Prior Publication Data
US 2020/0017650 A1 Jan. 16, 2020

Related U.S. Application Data

(60) Provisional application No. 62/478,210, filed on Mar. 29, 2017.

(51) Int. Cl.
| A61L 15/60 | (2006.01) |
| C08J 3/075 | (2006.01) |
| C08J 7/06 | (2006.01) |
| C09D 4/00 | (2006.01) |
| C08J 7/056 | (2020.01) |

(52) U.S. Cl.
CPC .............. *A61L 15/60* (2013.01); *C08J 3/075* (2013.01); *C08J 7/056* (2020.01); *C08J 7/065* (2013.01); *C09D 4/00* (2013.01); *C08J 2375/04* (2013.01); *C08J 2433/26* (2013.01)

(58) Field of Classification Search
None
See application file for complete search history.

(56) References Cited

U.S. PATENT DOCUMENTS

| 5,209,849 | A | 5/1993 | Hu |
| 5,672,656 | A | 9/1997 | Murayama |
| 5,776,611 | A | 7/1998 | Elton |
| 6,943,206 | B2 | 9/2005 | Haraguchi |
| 7,696,259 | B2 | 4/2010 | Hanley |
| 7,993,892 | B2 | 8/2011 | Takada |
| 8,283,612 | B2 | 10/2012 | Keite-Telgenbuescher |
| 8,841,354 | B2 | 9/2014 | Nielson |
| 8,957,125 | B2 | 2/2015 | Belt |
| 9,034,941 | B2 | 5/2015 | Nielson |
| 9,212,266 | B2 | 12/2015 | Nielson |
| 2006/0148352 | A1 | 7/2006 | Munro |
| 2010/0198168 | A1 | 8/2010 | Rooijmans |
| 2011/0059874 | A1 | 3/2011 | Rooijmans |
| 2012/0035294 | A1 | 2/2012 | Kim |
| 2015/0352259 | A1* | 12/2015 | Room ............... C08G 65/3322 428/474.4 |
| 2016/0046825 | A1* | 2/2016 | Hood .................... B65D 65/42 428/413 |

FOREIGN PATENT DOCUMENTS

| CN | 85101480 | 1/1987 |
| CN | 101848565 | 9/2010 |
| CN | 101942167 | 1/2011 |
| CN | 102850477 | 1/2013 |
| EP | 1 829 896 | 9/2007 |
| GB | 2464080 | 4/2010 |
| JP | 2006-169314 | 6/2006 |
| JP | 2007-126572 | 5/2007 |
| JP | 2011-213793 | 10/2011 |
| WO | WO 2000-073596 | 12/2000 |
| WO | WO 2012-144332 | 10/2012 |
| WO | WO 2013-027051 | 2/2013 |
| WO | WO 2014-118382 | 8/2014 |
| WO | WO 2017-058698 | 4/2017 |
| WO | WO 2017-223544 | 12/2017 |

OTHER PUBLICATIONS

Bordes, "Nano-Biocomposites: Biodegradable Polyester/Nanoclay Systems" Progress in Polymer Science, Feb. 2009, vol. 34, No. 2, pp. 125-155.
Cui, "Synthetically Simple, Highly Resilient Hydrogels", Biomacromolecules, Feb. 2012, vol. 13, No. 3, pp. 584-588.
Drtina, Highly Cross-Linked Azlactone Functional Supports of Tailorable Polarity, Macromolecules, Jun. 1996, vol. 29, No. 13, pp. 4486-4489.
Fall, "Shear Thickening of Laponite Suspensions with Poly(ethylene oxide)", Soft Matter, Mar. 2012, vol. 8, No. 17, pp. 4645-4651.
Gong, "Double-Network Hydrogels with Extremely High Mechanical Strength", Advanced Materials, Jul. 2003, vol. 15 No.14, pp. 1155-1158.
Gutierrez-Villarreal, "Surface Graft Polymerization of N-Vinylcaprolactam onto Polylactic Acid Film by UV Irradiation", Journal of Polymer Research, Jun. 2013, vol. 20, No. 149, pp. 1-6.
Haraguchi, "Compositional Effects on Mechanical Properties of Nanocomposite Hydrogels Composed of Poly(N,N-dimethylacrylamide) and Clay", Macromolecules, Jul. 2003, vol. 36, No. 15, pp. 5732-5741.

(Continued)

*Primary Examiner* — Jeffrey D Washville
(74) *Attorney, Agent, or Firm* — Julie Lapos-Kuchar

(57) ABSTRACT

Described herein is a hydrogel-containing multilayer article and methods of making, said hydrogel-containing multilayer article comprising: (i) a polymeric substrate comprising an abstractable atom; and (ii) a cured aqueous coating composition thereon wherein the coating composition comprises: (a) a hydrophilic monomer comprising a (meth)acrylamide, (meth)acrylate, and combinations thereof: (b) at least 2 wt % of a water-swellable clay; (c) a water-soluble type I photoinitiator; and (d) an acid or salt wherein a water insoluble type II photoinitiator is localized at the interface between the hydrogel coating and the polymeric substrate.

20 Claims, No Drawings

(56) References Cited

OTHER PUBLICATIONS

Haraguchi, "Mechanism of Forming Organic/Inorganic Network Structures during In-situ Free-Radical Polymerization in PNIPA-Clay Nanocomposite Hydrogels", Macromolecules, Apr. 2005, vol. 38, No. 8, pp. 3482-3490.
Haraguchi, Novel Manufacturing Process of Nanocomposite Hydrogel for Bio-Applications, ASME 2005 International Mechanical Engineering Congress and Exposition, Nov. 2005, pp. 119-126.
Joshi, "Rheological Behaviour of Aqueous Suspensions of Laponite: New Insights into the Ageing Phenomena", Proceedings of the Royal Society A: Mathematical, Physical and Engineering Science, Dec. 2007, vol. 464, No. 2090, 27 pages.
Pandiyarajan, "Influence of the Molecular Structure of Surface-Attached Poly (N-alkyl Acrylamide) Coatings on the Interaction of Surfaces with Proteins, Cells and Blood Platelets"" Macromolecular Bioscience, Jul. 2013, vol. 13, No. 7, pp. 873-884.
Ranby, "Surface Modification and Lamination of Polymers by Photografting" International Journal of Adhesion and Adhesives, Oct. 1999, vol. 19, No. 5, pp. 337-343.
Ranby "Surface Photografting of Polymer Fibers, Films and Sheets", Nuclear Instruments and Methods in Physics Research Section B: Beam Interactions with Materials and Atoms, May 1999, vol. 151, No. 1-4, pp. 301-305.
Ruckert, "Surface Modification of Polymers-IV. Grafting of Acrylamide Via An Unexpected Mechanism Using A Water Soluble Photo-Initiator", European Polymer Journal, Feb. 1996, vol. 32, No. 2, pp. 201-208.
Tretinnikov, "Benzophenone-Initiated Grafting Photopolymerization of Acrylic Acid on the Surface of Polyethylene from the Monomer Aqueous Solution without Its Deaeration", Polymer Science Series B, Sep. 2012, vol. 54, No. 9-10, pp. 427-433.
Tuncaboylu, "Structure Optimization of Self-Healing Hydrogels Formed via Hydrophobic Interactions", Polymer, Nov. 2012, vol. 53, No. 24, pp. 5513-5522.
Wang, Large Deformation Behavior and Effective Network Chain Density of Swollen Poly(N-isopropylacrylamide)-Laponite Nanocomposite Hydrogels, Soft Matter, Nov. 2012, vol. 8, No. 3, pp. 774-783.
Yang, "Surface Hydrophilization of Microporous Polypropylene Membrane by Grafting Zwitterionic Polymer for Anti-Biofouling", Journal of Membrane Science, Oct. 2010, vol. 362, No. 1-2, pp. 255-264.
International Search Report for PCT International Application No. PCT/US2018/023914, dated Jun. 22, 2018, 6 pages.

* cited by examiner

HYDROGEL COMPOSITIONS BONDED TO POLYMERIC SUBSTRATES

CROSS REFERENCE TO RELATED APPLICATIONS

This application is a national stage filing under 35 U.S.C. 371 of PCT/US2018/023914, filed Mar. 23, 2018, which claims the benefit of U.S. Application No. 62/478,210, filed Mar. 29, 2017, the disclosure of which is incorporated by reference in its/their entirety herein.

TECHNICAL FIELD

Hydrogel compositions bonded to polymeric substrates are disclosed.

BACKGROUND

Wounds or lesions typically exude liquid material after formation and during the healing process. When selecting a dressing, a balance needs to be struck between the desire to remove exudate from the wound and maintaining an appropriate level of fluid in and around the wound to prevent it becoming too dry or too wet.

Hydrogels have been increasingly used in wound care because of their ability to absorb water and keep the wound in a suitably moist condition, which promotes healing.

Hydrogels are hydrophilic polymers characterized by their hydrophilicity (i.e., capacity to absorb large amounts of fluid such as wound exudate) and insolubility in water (i.e. they are capable of swelling in water while generally preserving their shape). The hydrophilicity is generally due to groups such as hydroxyl, carboxy, carboxamido, and esters, among others. On contact with water, the hydrogel assumes a swollen hydrated state that results from a balance between the dispersing forces acting on hydrated chains and cohesive forces that do not prevent the penetration of water into the polymer network. The cohesive forces are most often the result of covalent crosslinking, but additionally may result from electrostatic, hydrophobic or dipole-dipole interactions.

Most hydrogels used for wound care are non-adhesive and thus, must be secured into a backing layer with either an adhesive to fixedly attach the hydrogel onto the backing layer and/or through the use of a netting placed between the wound and the hydrogel such as disclosed in U.S. Pat. Publ. No 2006/0148352 (Munro et al.). Adhesive hydrogels can be used, however, once in contact with the wound exudate or other aqueous solutions, the hydrogel imbibes water. This can reduce the hydrogel's tackiness and thus, diminish or eliminate adhesion between the hydrogel and the backing layer.

SUMMARY

There is a desire for identifying an alternative means of robustly adhering hydrogels onto a polymeric substrate.

In one aspect, a method of making a grafted hydrogel is described. The method comprising the steps in the order of:
(a) obtaining a polymeric substrate having an abstractable atom;
(b) coating the polymeric substrate with a Type II photoinitiator to form a dried coated substrate;
(c) applying an aqueous composition to form an aqueous coated substrate, wherein the aqueous composition comprises (i) a hydrophilic monomer comprising a (meth)acrylamide, (meth)acrylate, and combinations thereof; (ii) 2-20% wt water-swellable clay; and (iii) a water soluble type I photoinitiator, and (iv) a salt or acid;
(d) curing the aqueous coated substrate.

In another aspect, a multilayer article is disclosed comprising:
(i) a polymeric substrate comprising an abstractable atom; and
(ii) a hydrogel coating thereon wherein the hydrogel coating has a water content of at least 10 wt % and is covalently bonded to the polymer substrate, and wherein the hydrogel coating is derived from an aqueous composition comprising:
(a) a hydrophilic monomer comprising a (meth)acrylamide, (meth)acrylate, and combinations thereof;
(b) at least 2 wt % of a water-swellable clay;
(c) a water-soluble type I photoinitiator; and
(d) an acid or salt,
wherein a water insoluble type II photoinitiator is localized at the interface between the hydrogel coating and the polymeric substrate.

The above summary is not intended to describe each embodiment. The details of one or more embodiments of the invention are also set forth in the description below. Other features, objects, and advantages will be apparent from the description and from the claims.

DETAILED DESCRIPTION

As used herein, the term
"a", "an", and "the" are used interchangeably and mean one or more; and
"and/or" is used to indicate one or both stated cases may occur, for example A and/or B includes, (A and B) and (A or B);
"(meth)acrylate" refers to compounds containing either an acrylate or a methacrylate structure or combinations thereof;
"(meth)acrylamide" refers to compounds containing either an acrylamide or a methacrylamide structure or combinations thereof; and
"monomer" is a molecule which can undergo polymerization which then forms part of the essential structure of a polymer.

Also herein, recitation of ranges by endpoints includes all numbers subsumed within that range (e.g., 1 to 10 includes 1.4, 1.9, 2.33, 5.75, 9.98, etc.).

Also herein, recitation of "at least one" includes all numbers of one and greater (e.g., at least 2, at least 4, at least 6, at least 8, at least 10, at least 25, at least 50, at least 100, etc.).

A hydrogel is a network of hydrophilic polymer chains, which are dispersed in an aqueous medium. The water-swollen polymeric networks are rendered insoluble due to interactions (e.g., crosslinks) between polymer chains. When this network of hydrophilic polymers is placed in an aqueous solution, these systems often imbibe water until they reach an equilibrium swelling point. At this point, the enthalpy of mixing equals the restrictions imposed by the interactions (e.g., covalent bonding between chains, or non-covalent interactions (H-bonding, electrostatic, van der Waals) between chains) that hold the polymer chains together.

A hydrogel has the capacity to absorb many times (e.g. at least about 2.5, 5, 10, or even 50 times, and potentially up to about 250 times) its own weight of exudate or other fluid (e.g. water) in 24 hours.

Typically, the covalent attachment of hydrogels onto substrates is described with glass substrates, where bonds formed between glass and alkoxysilyl-containing reactive monomers are utilized. Once the alkoxysilyl groups of the monomer have reacted with and formed a bond with the glass substrate, the reactive pendant group on the monomer can be utilized to initiate polymerization of a network hydrogel. This attachment method is dependent on the inherent reactivity of the glass substrate. In the case of polymeric substrates, such as films based on polyolefins, polyurethanes, and polyesters, the substrate surface does not have the required innate reactivity for easy modification. The present disclosure is directed toward a method for the durable attachment (e.g., covalent attachment) of a hydrogel composition onto a polymeric substrate and articles therefrom.

In the present disclosure a Type II photoinitiator is applied onto the polymeric substrate followed by coating with an aqueous composition. The aqueous coating composition is then cured to form a hydrogel, which has durable attachment to the polymeric substrate.

The substrates of the present disclosure are organic polymeric substrates, more specifically a polymeric substrate comprising an abstractable atom, typically, a hydrogen atom.

Exemplary polymeric substrates include polyamides such as nylons, polyesters such as polyethylene terephthalate (PET), polyolefins such as polypropylene, and polyurethanes.

In one embodiment, the polymeric substrate is flexible, meaning that the polymeric substrate can bend at least 5, 10 or even 15 degrees from a plane which is parallel to a major surface of the polymeric substrate. In one embodiment, the polymeric substrate conforms to a curved surface.

In one embodiment, the polymeric substrate may be cleaned or treated prior to contact with the photoinitiator. Such methods are known in the art and include: solvent cleaning, plasma treatment, corona treatment, etc.

Photoinitiators for radical polymerization are classified in the art as cleavage (Type I) and hydrogen-abstraction (Type II) initiators. A Type I initiator, upon absorption of light, spontaneously undergoes "α-cleavage", yielding the initiating radical immediately. A Type II initiator is a photoinitiator which, when activated by actinic radiation, forms free radicals by hydrogen abstraction from a second (H-donor) compound to generate the actual initiating free radical. This second compound is called a polymerization synergist or co-initiator.

In the present disclosure, a Type II photoinitiator is first applied to at least a first major surface of the polymeric substrate in the absence of a monomer. In other words, an olefinic compound, which can polymerize, is not co-applied with the Type II photoinitiator. Although not wanting to be limited by theory, it is believed that in the present disclosure, when activated with actinic radiation, the Type II photoinitiator abstracts a hydrogen from the polymeric substrate, leaving a radical site, which can then react with the monomers in the subsequently applied aqueous composition to covalently bond the hydrogel to the polymeric substrate. Coating of the Type II photoinitiator on the surface of the substrate increases the frequency of hydrogen abstraction from the polymeric substrate, and thus increases the adhesion of the hydrogel to the polymeric substrate.

In one embodiment, the Type II photoinitiator is applied as a liquid, wherein the Type II photoinitiator is dissolved and/or dispersed in a solvent, herein referred to as the Type II photoinitiator composition. In one embodiment, the Type II photoinitiator composition consists essentially of the Type II photoinitiator, meaning that the Type II photoinitiator composition is substantially free of a monomer (i.e., less than 0.1, 0.01 or even 0.001% by weight or even no monomer) but may comprise solvent or other materials, which do not attach the hydrogel coating to the polymeric substrate. The solvent of the Type II photoinitiator composition is not particularly limited. Exemplary solvents include: alcohols (such as propanol, methanol, and ethanol), aliphatic or aromatic hydrocarbons (such as hexane, heptane, cyclohexane, pentane, and toluene), esters, ketones (such as acetone), and/or ethers. In one embodiment, the Type II photoinitiator composition comprises at least 0.1, 0.25, 0.5, 1, 2, 3, 4, or even 5 wt (weight) % and at most 8, 10, 12, 15, or even 20 wt % of the Type II photoinitiator. If applied as a liquid, the Type II photoinitiator composition is typically applied as a dilute solution in solvent directly onto the polymeric substrate and then substantially dried to remove the solvent such that a layer of dried Type II photoinitiator is present on the surface of the polymeric substrate. Substantially dried means less than about 5, 4, 2, 1, or even 0.5% by weight of the dried coating is residual solvent. The Type II photoinitiator composition is dried prior to the application of the aqueous composition to minimize the diffusion of the Type II photoinitiator away from the surface of the polymeric substrate during subsequent coating of the aqueous composition.

Alternatively, the Type II photoinitiator may be applied in a solvent-free form, such as by coating onto the surface of the polymeric substrate by vacuum deposition, for example, by thermal evaporation or by sputtering, as is known in the art.

In one embodiment, the Type II photoinitiator is water insoluble. Water insoluble refers to the amount of the photoinitiator that dissolves in deionized water being 0.5% by weight or less.

In one embodiment, the Type II photoinitiator comprises substituents on 2, 3 and/or 4 position of the phenyl rings in the Type II photoinitiator, preferably on the 3 and/or 4 position of the phenyl rings. Examples of substituents are substituents comprising hydroxy, anhydride, acid, ester, ether, amide and amino functional groups. Examples of Type II photoinitiators include benzophenone, 2-benzoyl benzoic acid, 3-benzoyl benzoic acid, 4-benzoyl benzoic acid, 3,3', 4,4'-benzophenone tetracarboxylic acid, Michler's ketone, benzil, anthraquinone, 5,12-naphthacenequinone, aceanthracenequinone, benz(A)anthracene-7,12-dione, 1,4-chrysenequinone, 6,13-pentacenequinone, 5,7,12,14-pentacenetetrone, 9-fluorenone, anthrone, xanthone, thioxanthone, acridone, dibenzosuberone, acetophenone, and chromone.

The polymeric substrate comprising a dried layer of Type II photoinitiator is then coated with the aqueous solution, which is cured to form the hydrogel coating.

The hydrogel coating of the present disclosure has a water content of at least 10, 15, 20, 30, 40, or even 50 wt %. The hydrogel coating is derived from an aqueous composition comprising at least one hydrophilic monomer, a water-swellable clay, a water-soluble photoinitiator, and an acid and/or salt. In one embodiment of the present disclosure, the hydrogel coating disclosed herein, after absorbing exudate or other fluids, remains attached to the polymeric substrate.

The hydrophilic monomer is a monomer that is soluble in water and/or is soluble in mixed solution comprising organic solvents miscible with water, having water as the main component. In one embodiment, the monomer has a lipophilicity index less than or equal to 20. As used herein, the term "lipophilicity index" or "LI" refers to an index for characterizing the hydrophobic or hydrophilic character of a monomer. The lipophilicity index is determined by partitioning a monomer in equal volumes (1:1) of a non-polar solvent (e.g., hexane) and a polar solvent (e.g., a 75:25 acetonitrile-water solution). The lipophilicity index is equal to the weight percent of the monomer remaining in the non-polar phase after partitioning. Monomers that are more hydrophobic tend to have a higher lipophilicity index; similarly, monomers that are more hydrophilic tend to have a lower lipophilicity index. Measurement of lipophilicity index is further described in Drtina et al., *Macromolecules*, 29, 4486-4489 (1996). Examples of non-ionic monomers that have a sufficiently low lipophilicity index include, but are not limited to, hydroxyalkyl(meth)acrylates such as 2-hydroxyethylacrylate, 3-hydroxypropylacrylate, 2-hydroxyethylmethacrylate (e.g., LI is 1), and 3-hydroxypropylmethacrylate (e.g., LI is 2); acrylamide (e.g., LI is less than 1) and methacrylamide (LI is less than 1); glycerol monomethacrylate and glycerol monoacrylate; N-alkyl (meth)acrylamides such as N-methylacrylamide (e.g., LI is less than 1), N,N-dimethylacrylamide (e.g., LI is less than 1), N-methylmethacrylamide, and N,N-dimethylmethacrylamide; N-vinylamides such as N-vinylformamide, N-vinylacetamide, and N-vinylpyrrolidone; acetoxyalky(meth)acrylates such as 2-acetoxyethylacrylate and 2-acetoxyethylmethacrylate (e.g., LI is 9); glycidyl(meth) acrylates such as glycidylacrylate and glycidylmethacrylate (e.g., LI is 11); and vinylalkylazlactones such as vinyldimethylazlactone (e.g., LI is 15).

Hydrophilic monomers are known in the art and include vinyl monomers such as (meth)acrylates, and (meth)acrylamides.

Exemplary (meth)acrylate monomers include: acrylic acid (3-sulphopropyl) ester (SPA) and salts thereof, N,N-dimethylaminoethylmethacrylate and salts thereof, [2-(methacryloyloxy)ethyl]dimethyl-(3-sulfopropyl) ammonium hydroxide, [2-(methacryloyloxy)ethyl] trimethylammonium chloride, 2-hydroxyethyl(meth) acrylate, hydroxypropyl(meth)acrylate, and polyethyleneglycolmono(meth)acrylate.

Exemplary (meth)acrylamide monomers include: N-substituted (meth)acrylamide derivatives, such as N-methylacrylamide, N-ethylacrylamide, cyclopropylacrylamide, N-isopropylmethacrylamide, N-methylmethacrylamide, cyclopropyimethacrylamide, N-isopropylmethacrylamide, diacetone acrylamide, hydroxyethyl acrylamide, 2-acrylamido-2-methylpropane sulphonic acid (AMPS) and salts thereof; and N,N-di-substituted (meth)acrylamide derivatives, such as N,N-dimethylacrylamide, N,N-dimethylaminopropylacrylamide, N-methyl-N-ethylacrylamide, N-methyl-N-isopropylacrylamide, N-methyl-N-n-propylacrylamide, N,N-diethylacrylamide, N-acryloylpyrrolidine, N-acryloylpiperidine, N-acryloyl N' methylhomopiperidine, and N-acryloyl-N'-methylpiperidine, N-acryloyl morpholine or a substituted derivative thereof and N,N dimethylaminopropylmethacrylamide.

Other useful water soluble monomers include vinyl amides such as N-vinylacetamide, N-vinylformamide, N-vinylpyrrolidinone, and vinylpyridine.

In one embodiment, the vinyl monomers are substituted with acid or ionic groups (which may, for example, be salts of acid groups or tertiary ammonium groups). Such salts may include, for example, sodium, potassium, lithium, cesium, calcium, magnesium, zinc or ammonium salts or mixtures thereof. In one embodiment, the vinyl monomers comprise pendant sulphonic acid groups, and/or carboxylic acid groups.

The hydrophilic monomers optionally include conventional crosslinking agents (i.e., compounds which covalently-bond polymer chains together), which are suitably used to provide the necessary mechanical stability and optionally to control the adhesive properties of the hydrogel and/or tune the modulus of the hydrogel. The amount of crosslinking agent required will be readily apparent to those skilled in the art such as from about 0.01, 0.05, or even 0.08% to about 0.5, 0.4, or even 0.3% by weight of the aqueous composition. Typical crosslinking agents comprise at least two polymerizable double bonds, and include tripropylene glycol diacrylate, ethylene glycol dimethacrylate, polyethylene glycol diacrylate (polyethylene glycol (PEG) molecular weight between about 100 and about 4000, for example PEG400 or PEG600), and methylene bisacrylamide (MBA). In one embodiment, the composition is substantially free (i.e., less than 0.01, or even 0.001 wt %) of conventional crosslinking agents as in known in the art and disclosed, for example, in Haraguchi et al. in Macromolecules v. 36 (2003) p. 5732-5741.

The hydrophilic monomers in the present disclosure are preferably interactive with the water-swellable clay, when polymerized. Preferably, some of the hydrophilic monomers have functional groups which can form hydrogen bonds, ionic bonds, and coordinate bonds, and covalent bonds with the water-swellable clay. Examples of such functional groups include an amide group, an amino group, a hydroxy group, a tetramethyl ammonium group, a silanol group, and an epoxy group.

Clay is typically added to a hydrogel composition to enhance the mechanical properties in the composites comprising large amounts of water. The water-swellable clay of the present disclosure, is a clay mineral capable of swelling and uniformly dispersing in water or a mixed solvent of water and an organic solvent. In one embodiment, the water-swellable clay is an inorganic clay mineral capable of uniformly dispersing in a molecular form (single layer) or level close thereto in water, More specifically, the water-swellable clay may contain sodium as an interlayer ion. Exemplary water-swellable clays include: synthetic hectorite [$Na_{0.3}(Mg,Li)_3Si_4O_{10}(OH)_2$], saponite [$Ca_{0.25}(Mg,Fe)_3((Si,Al)_4O_{10}(OH)_2.n(H_2O)$], montmorillonite [$(Na,Ca)_{0.33}(Al,Mg)_2(Si_4O_{10})(OH)_2.nH_2O$], laponite [$Na^{+0.07}[(Si_3Mg_{5.5}Li_{0.3})O_{20}(OH)_4]^{-0.07}$], monitrite, and synthetic mica.

The aqueous compositions of the present disclosure comprise at least 2% wt of the water-swellable clay versus the total weight of the aqueous composition. In one embodiment, the amount of water-swellable clay in the aqueous composition is more than 2, 4, or even 5 wt %; and less than 10, 15, or even 20 wt % versus the total weight of the aqueous composition.

The aqueous composition of the present disclosure comprises a Type I photoinitiator; and optionally a Type II photoinitiator.

In the present disclosure, the Type I photoinitiator is water-soluble, which means that at ambient conditions (e.g., 23° C.), the photoinitiator has a solubility of at least 0.01, 0.1, 0.25, 0.5, 1, 2, 5 or even 8% by weight in deionized water. If the solubility of the photoinitiator in water is too low, the photoinitiator will not be available for efficient radical generation.

Commercially available Type I and Type II photoinitiators may not have sufficient water solubility to be used in the aqueous hydrogel compositions of the present disclosure. To improve the solubility of the photoinitiator, as is known in the art, the photoinitiator can be derivatized with a (more) hydrophilic group, the counter ion can be adjusted to improve the compound's water solubility, and/or a co-solvent can be used to aid the dissolution of the photoinitiator in the aqueous composition.

Examples of Type I photoinitiators are benzoin derivatives, methylolbenzoin and 4-benzoyl-1,3-dioxolane derivatives, benzilketals, α,α-dialkoxyacetophenones, α-hydroxy alkylphenones, α-aminoalkylphenones, acylphosphine oxides, bisacylphosphine oxides, acylphosphine sulphides, halogenated acetophenone derivatives, and the like. Exemplary water-soluble Type I photoinitiators include: 4-[2-(4-morpholino)benzoyl-2-dimethylamino]-butylbenzene-sulfonate salt, and phenyl-2,4,6-trimethyl-benzoylphosphinate salt. Suitable salts include, for example, sodium and lithium cations. A commercial example of suitable water-soluble Type I photoinitiator is available from BASF SE, Ludwigshafen, Germany, under the trade designation: "IRGACURE 2959" (2-hydroxy-4'-(2-hydroxyethoxy)-2-methyl propiophenone).

Examples of Type II photoinitiators are modified benzophenones, benzils, and thioxanthones.

Exemplary Type II photoinitiators include those of the structure:

Formula (I)

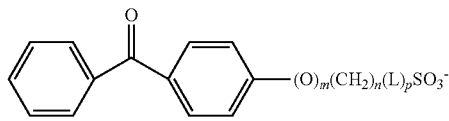

where m is 0 or 1; n is 1, 2, 3, or 4; p is 0 or 1; and L is an alkylene group comprising from 1 to 4 carbons and having a hydroxyl group. In one embodiment, L is —CH(OH)CH$_2$—. Exemplary photoinitiators of include:

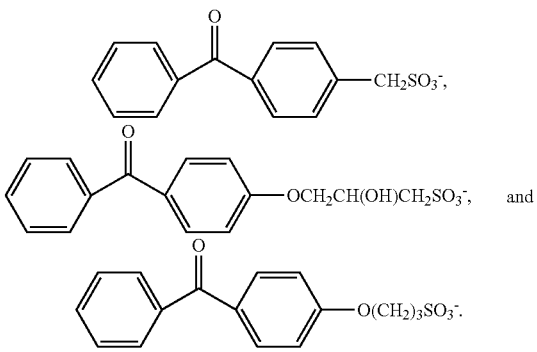

Examples of Type II photoinitiators include those of the structure:

Formula (II)

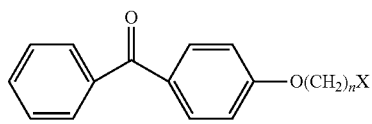

where n is 1, 2, 3, or 4; and X is selected from —N(CH$_3$)$_3$SO$_4$CH$_3$, and —CH(OH)—(CH$_2$)$_p$—N(CH$_3$)$_3$Cl where p is 1, 2, 3, or 4. Exemplary photoinitiators of Formula (II) include:

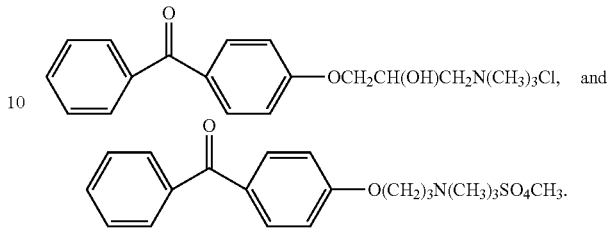

Examples of Type II photoinitiators include those of the structure:

Formula (III)

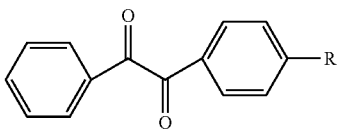

wherein R is -alkyl sulfonate comprising 1, 2, 3, or 4 carbon atoms (e.g., CH$_2$SO$_3$Na) or a tertiary amine salt comprising at 3, 4, 5, 6, or even 7 carbon atoms (e.g., —CH$_2$N(CH$_3$)$_3$Cl).

Examples of Type II photoinitiators include those of the structure:

Formula (IV)

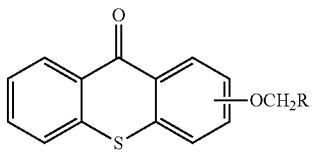

wherein R comprises a carboxylic acid or a tertiary amine and salts thereof. Exemplary R groups include —COOH, or —CH(OH)CH$_2$N(CH$_3$)$_3$Cl.

An example of Type II photoinitiator include that of the structure

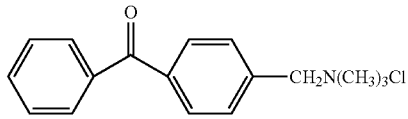

Exemplary water-soluble Type II photoinitiators include: 4-(3-sulfopropyloxy)benzophenone; 2-(3-sulfopropyloxy)thioxanthene-9-one; and 2-, 3-, and 4-carboxybenzophenone.

In one embodiment, the aqueous composition comprises at least 0.01, 0.05, 0.1, or even 0.5 wt %; and at most 1, 2, 4, or even 5 wt % of the Type I initiator based on the total weight of the aqueous composition.

In one embodiment, the aqueous composition is substantially free of a Type II photoinitiator, meaning that the aqueous composition comprises less than 0.1, or even 0.01 wt % of a Type II photoinitiator.

If a Type II initiator is used in the aqueous composition, in one embodiment, the aqueous composition comprises at least 0.01, 0.05, 0.1, 0.2, or even 0.5 wt %; and at most 1, 2, 4, or even 5 wt % of the Type II initiator based on the total weight of the aqueous composition.

In addition to the hydrophilic monomer, water-swellable clay, and water soluble Type I photoinitiator, the aqueous composition further comprises a salt and/or an acid. The ions of the salt and/or acid may be used to modify the viscosity of the aqueous composition. In one embodiment, these salts and/or acids are the hydrophilic monomers substituted with acid or ionic groups as described above. In one embodiment, an acid added to the aqueous composition. Exemplary acids include: mineral acids (such as hydrochloric acid, nitric acid, and sulfuric acid) or organic acids (such as citric acid, ascorbic acid, acetic acid, propanoic acid, lactic acid, succinic acid, tartaric acid, and benzoic acid). In one embodiment, a salt is added to the aqueous composition. Exemplary salts include those comprising an alkali metal (e.g., Na or K), alkaline earth metal (e.g., Mg or Ca), a chloride ion, a bromide ion, an iodide ion, or an ammonium ion. Exemplary salts include salts of the aforementioned acids, such as sodium sulfate, ammonium sulfate, sodium chloride, potassium chloride, magnesium chloride. Exemplary salts may also include ammonium persulfate and sodium persulfate. In one embodiment, the aqueous composition comprises at least 0.001, 0.01, 0.1 or even 1% wt of acid and/or salt.

The pH can be adjusted to make the hydrogel more compatible with biological applications and/or to improve the durability of the bonding between the hydrogel coating and the polymeric substrate. In one embodiment, the pH of the aqueous composition is maintained at a pH of at least 5, 5.5, 6, or even 6.5; and at most 7.5, 8, 8.5, 9, or even 9.5.

The aqueous composition of the present disclosure may include one or more additional ingredients, which may be added prior to the curing (i.e., polymerization, grafting, and/or crosslinking) of the aqueous composition or after curing to impact the aesthetics and/or performance of the resulting hydrogel coating. It is generally preferred that substantially all of the final ingredients of the hydrogel are present in the aqueous composition, and that—apart from minor conventional conditioning or, in some cases, subsequent modifications caused by the sterilization procedure— substantially no chemical modification of the hydrogel takes place after completion of the polymerization reaction.

Such additional ingredients are selected from additives known in the art, including, for example, water, organic plasticizers, surfactants, polymeric material (hydrophobic or hydrophilic in nature, including proteins, enzymes, naturally occurring polymers and gums), synthetic polymers with and without pendant carboxylic acids, electrolytes, osmolytes, pH regulators, colorants, chloride sources, bioactive compounds and mixtures thereof. In some embodiments, the additional ingredients may serve more than one purpose. For example, glycerol may serve as an organic plasticizer and an osmolyte.

In one embodiment, an additional polymer may be added. The polymer can be a natural polymer (e.g. xanthan gum), synthetic polymer (e.g. polyoxypropylene-polyoxyethylene block copolymer or poly-(methyl vinyl ether alt maleic anhydride)), or any combination thereof. In one embodiment, a rheology modifying polymer may be incorporated into the aqueous composition at levels typically up to about 10% by weight of total polymerization reaction mixture, e.g. from about 0.2% to about 10% by weight. Such polymer(s) may include polyacrylamide, poly-NaAMPS, polyethylene glycol (PEG), polyvinylpyrrolidone (PVP) or carboxymethyl cellulose.

In one embodiment, a bioactive compound may be added. The term "bioactive compounds" is used to mean any compound or mixture included within the hydrogel for some effect it has on living systems, whether the living system be bacteria or other microorganisms or higher animals such as the patient. Bioactive compounds that may be mentioned include, for example, pharmaceutically active compounds, antimicrobial agents, antiseptic agents, antibiotics and any combination thereof. The hydrogel may incorporate antimicrobial agents, for example, those active against such organisms as *Staphylococcus aureus* and *Pseudomonas aeruginosa*. Antimicrobial agents may, for example, include: sources of oxygen and/or iodine (e.g. hydrogen peroxide or a source thereof and/or an iodide salt such as potassium iodide); antimicrobial metals, metal ions and salts, such as, for example, silver-containing antimicrobial agents (e.g. colloidal silver, silver oxide, silver nitrate, silver thiosulphate, silver sulphadiazine, or any combination thereof), hypochlorous acid; or any combination thereof.

In one embodiment, agents for stimulating the healing of wounds and/or for restricting or preventing scarring may be incorporated into the hydrogel. Examples of such agents include growth factors such as TGF (transforming growth factor), PDGF (platelet derived growth factor), KGF (keratinocyte growth factor, e.g. KGF-I or KGF-2), VEGF (vascular endothelial growth factor), IGF (insulin growth factor, optionally in association with one or more of IGF binding protein and vitronectin); cell nutrients; glucose; an anabolic hormone or hormone mixture such as insulin, triiodothyronine, thyroxine or any combination thereof; or any combination thereof.

In one embodiment, the aqueous composition further comprises a humectant such as polyethylene glycol, polyethylene glycol-co-polypropylene oxide copolymers, partially hydrolyzed polyvinyl acetate, polyvinyl pyrrolidone, glycerol or glycerol derivative, methylcellulose or other cellulose derivative, polyoxazoline, and natural gums. The amount of humectant added can vary based on the type used. For example, typically no more than 30%, 40%, 50% or even 60% by wt of glycerol can be added.

In one embodiment, one or more plasticizers, preferably one or more organic plasticizer is added. The one or more organic plasticizer, when present, may suitably comprise any of the following either alone or in combination: at least one polyhydric alcohol (such as glycerol, polyethylene glycol, or sorbitol), at least one ester derived therefrom, at least one polymeric alcohol (such as polyethylene oxide) and/or at least one mono- or poly-alkylated derivative of a polyhydric or polymeric alcohol (such as alkylated polyethylene glycol). Glycerol is the preferred plasticizer. An alternative preferred plasticizer is the ester derived from boric acid and glycerol. When present, the organic plasticizer may comprise up to about 45%, for example up to about 35%, for example up to about 25%, for example up to about 15%, by weight of the hydrogel composition.

In one embodiment, the aqueous composition comprises a compatible surfactant. Surfactants can lower the surface tension of the mixture before polymerization and thus aid processing. The surfactant or surfactants may be non-ionic, anionic, zwitterionic or cationic, alone or in any mixture or combination. The surfactant may itself be reactive, i.e. capable of participating in the hydrogel-forming reaction. The total amount of surfactant, if present, is suitably up to about 10% by weight of the aqueous composition, preferably from about 0.05% to about 4% by weight. The surfactant may, for example, comprise at least one propylene oxide/ethylene oxide block copolymer, for example such as that supplied by BASF PLC under the trade name Pluronic P65 or L64.

Additional osmolyte(s) may be included to modify the osmolality of the hydrogel. Osmolytes may be ionic (e.g. electrolytes, for example salts which are readily soluble in the aqueous phase of the hydrogel to increase the ionic strength of selected cations or anions and hence the osmolality of the hydrogel). By selecting the ions present in an ionic osmolyte, and particularly by selecting the cation so as to correspond or not with cationic counterions in the monomer(s) of the hydrogel, the ionic strength of certain anions (e.g. chloride) can be varied with fine control, without substantially changing the ionic strength of cations already present in very large amounts as counterions of the monomer(s). Osmolytes may be organic (non-ionic), for example organic molecules which dissolve in or intimately mix with the aqueous phase of the hydrogel to increase the osmolality of the hydrogel deriving from non-ionic species in the aqueous phase. Such organic osmolytes include, for example, water-soluble sugars (e.g. glucose, fructose and other monosaccharides; sucrose, lactose, maltose and other disaccharides; or any combination of mono- and di-saccharides), polyhydric alcohols (e.g. glycerol and other polyhydroxylated alkanols).

In addition to water, in one embodiment a water miscible organic solvent may be used. Examples of such organic solvents include methanol, acetone, methyl ethyl ketone and tetrahydrofuran. The mixing ratio of water to the organic solvent can be optionally selected within a range wherein the water swelling clay can be homogeneously dispersed but the coated Type II initiator does not redissolve into the aqueous composition.

In one embodiment, the aqueous composition is substantially free of water miscible solvent, in other words, the aqueous composition comprises less than 5%, 1% or even 0.5% organic solvent versus the weight of the aqueous composition.

In one embodiment, the aqueous composition is substantially free of a C1-C5 alcohol. In other words, the aqueous composition comprises less than 5%, 2%, 1%, 0.5, or even 0.1% of an alcohol comprising 1, 2, 3, 4, or 5 carbon atoms.

The aqueous composition may be prepared using techniques known in the art. Briefly, the monomers, clay, water, initiators and any additional components may be added together.

The hydrogel may be formed in situ on the polymeric substrate. Additional layers may be added to the hydrogel coating and polymeric substrate construction to form desired articles, such as a wound dressing.

The aqueous composition containing the monomer(s) and preferably crosslinking agent, water, photoinitiator, acid and/or salt, and optionally other additional ingredients, is initially laid down on the polymeric substrate. Where the hydrogel composition is to be prepared in sheet form, the polymeric substrate will be a sheet. It may suitably comprise the backing layer or any desired sheet support member that may be interposed between the release layer and the hydrogel composition, or embedded within the hydrogel composition, in the finished dressing. In this way, the aqueous composition can be polymerized in situ, preferably with all or substantially all other components of the final dressing in place.

The aqueous composition can be coated onto the polymeric substrate using techniques known in the art. Exemplary coating methods include knife coating, bar coating, gravure coating, spray coating, etc.

The actinic radiation can be used to initiate reaction of the Type II photoinitiator located at the surface of the polymeric substrate and to cure the aqueous composition. These reactions may be done simultaneously or consecutively, wherein the Type II photoinitiator is first reacted to generate radicals on the surface of the polymeric substrate, following by coating with the aqueous composition, which then is subsequently cured to form the hydrogel. Actinic radiation includes for example, visible light or UV. Of these, ultraviolet rays are preferred in light of apparatus simplicity and handling convenience. The irradiation intensity of ultraviolet rays is preferably 1 to 500 mW/cm$^2$ and an irradiation period is generally 0.1 to 2000 seconds to cure the aqueous composition to form the hydrogel.

Any ultraviolet light source, as long as part of the emitted light can be absorbed by the photoinitiator or photoinitiator system, may be employed as a radiation source, such as, a high or low pressure mercury lamp, a cold cathode tube, a black light, an ultraviolet light emitting diode, an ultraviolet laser, and a flash light. Of these, the preferred source is one exhibiting a relatively long wavelength UV-contribution having a dominant wavelength of 300-400 nm. Specifically, a UV-A light source is preferred due to the reduced light scattering therewith resulting in more efficient interior curing. UV radiation is generally classed as UV-A, UV-B, and UV-C as follows: UV-A: 400 nm to 320 nm; UV-B: 320 nm to 290 nm; and UV-C: 290 nm to 100 nm.

Thickness of the resulting coating layer can vary depending on the application. For example, in in vivo applications (e.g., stents), the thickness of the coating layer can range from at least 10 nm or even 100 nm to at most 1 µm, 10 µm, or even 100 µm. For example, in wound care applications, the thickness of the coating layer can range from at least 0.1 mm, 0.25 mm, 0.5 mm, 1 mm or even 2 mm to at most 3 mm, 5 mm, or even 10 mm.

Because the hydrogel article of the present disclosure is made by first applying a Type II photoinitiator to the surface of the polymeric substrate before the aqueous composition, the resulting hydrogel article comprises a hydrogel coating directly contacting the polymeric substrate. In one embodiment, there is a Type II photoinitiator present at the interface between the hydrogel coating and the polymeric substrate. The Type II photoinitiator is discontinuous across this interface. In the case of using a water insoluble Type II photoinitiator to make the dried coated substrate, due to the lack of solubility of the Type II photoinitiator in the aqueous composition, the water insoluble Type II photoinitiator may be positioned near the interface between the hydrogel coating and the polymeric substrate. In other words, the water insoluble Type II photoinitiator is within 20, 15, 10, or even 5 nanometers from the first major surface of the polymeric substrate. In the case of using a water soluble Type II photoinitiator to make the dried coated substrate, the water soluble Type II photoinitiator may diffuse into the bulk of the hydrogel coating following curing depending on the photoinitiator and the crosslinking of the hydrogel.

In one embodiment of the present disclosure, the hydrogel coating is fixedly attached to the polymeric substrate. This attachment may be quantified by using a peel test, as described in the Example Section, wherein the amount of force to peel the hydrogel coating from the polymeric substrate at a 10 mm distance is at least 2 g, 5 g, 10 g, or even 15 g. In one embodiment, the force to peel the hydrogel coating from the polymeric substrate at a 30 mm distance is at least 10 g, 15 g, 20 g, 25 g, 50 g, or even 60 g.

After completion of the polymerization, the hydrogel-containing multilayer article is preferably sterilized in a conventional manner. The sterile composite may be used immediately, e.g. to provide a skin-adhesive layer in an article, or a top release layer may be applied to the composite for storage and transportation of the composite.

In one embodiment, the multilayer articles of the present disclosure are transparent.

The water content absorbed by the resulting hydrogel can be a function of the monomers used, for example HEMA and vinyl pyrrolidone and glycerol methacrylate and acrylamide monomers have been used form hydrogels with high water content. Acid-containing monomers such as (meth)acrylic acid and 2-acrylamido-2-methylpropanesulfonic acid provide ionic character at pH above 4 and contribute to large amounts of water absorption.

The hydrogel sheet may be part of a multi-layer composite, including further layers such as further hydrogels and/or other polymers and/or other sheet support members. For example, a breathable (air and/or moisture permeable) polymeric film (e.g. of polyurethane), which may if desired be present as a foam, may overlie the hydrogel sheet or composite on the major face of the sheet or composite directed away from the lesion in use. The breathable polymeric film may be, or may constitute part of, the backing layer.

The hydrogel composition and other sheet components as desired may preferably be provided with a release layer (e.g. of non-stick paper or plastic, such as siliconized paper or plastic) to protect one or both major face of the sheet prior to use.

Because of their high water content, hydrogels are often inherently biocompatible. Thus, these articles may be used in wound dressings or in devices/articles meant for contact with biological tissues.

A non-limiting list of exemplary embodiments and combinations of exemplary embodiments of the present disclosure are disclosed below.

Embodiment 1

A method of making a grafted hydrogel comprising the steps in the order of:
(a) obtaining a polymeric substrate having an abstractable atom;
(b) coating the polymeric substrate with a Type II photoinitiator to form a dried coated substrate;
(c) applying an aqueous composition to form an aqueous coated substrate, wherein the aqueous composition, wherein the aqueous composition comprises (i) a hydrophilic monomer comprising a (meth)acrylamide, (meth)acrylate, and combinations thereof; (ii) 2-20% wt water-swellable clay, and (iii) a water soluble Type I photoinitiator, and (iv) a salt or acid;
(d) curing the aqueous coated substrate.

Embodiment 2

The method of embodiment 1, wherein the polymeric substrate comprises at least one of polyolefin, polyurethanes, polyamide, and polyester.

Embodiment 3

The method of any one of the previous embodiments, wherein the polymeric substrate is flexible.

Embodiment 4

The method of any one of the previous embodiments, wherein the polymeric substrate is coated with a water insoluble Type II photoinitiator.

Embodiment 5

The method of embodiment 4, wherein the water insoluble Type II photoinitiator comprises at least one of: benzophenone, xanthone, thioxanthone, Michler's ketone, benzil, and anthraquinone.

Embodiment 6

The method of any one of the previous embodiments, wherein step (b) is performed by coating a liquid comprising the Type II photoinitiator and a solvent onto the polymeric substrate followed by removing the solvent to form the dried coated substrate.

Embodiment 7

The method of embodiment 6, wherein the solvent comprises at least one of: hexane, heptane, cyclohexane, pentane, ethanol, methanol, isopropanol, acetone, and toluene.

Embodiment 8

The method of any one of embodiments 6 and 7, wherein the liquid comprises at least 0.1 wt % of water insoluble Type II photoinitiator.

Embodiment 9

The method of any one of embodiments 6-8, wherein the liquid consists essentially of the Type II photoinitiator and the solvent.

Embodiment 10

The method of any one of the previous embodiments, wherein the aqueous solution comprises at least 20% solids.

Embodiment 11

The method of any one of the previous embodiments, wherein the aqueous composition intimately contacts the dried coated substrate.

Embodiment 12

The method of any one of the previous embodiments, wherein the aqueous composition comprises 0.001 to 5% by weight of the water soluble Type I photoinitiator.

Embodiment 13

The method of any one of the previous embodiments, wherein the water soluble Type I photoinitiator is 2-hydroxy-4'-(2-hydroxyethoxy)-2-methyl propiophenone.

Embodiment 14

The method of any one of the previous embodiments, wherein the aqueous composition is substantially free of a C1-C5 alcohol.

Embodiment 15

The method of any one of the previous embodiments, wherein the aqueous composition is substantially free of a Type II initiator.

Embodiment 16

The method of any one of the previous embodiments, wherein the aqueous composition has a pH of greater than 5 and less than 9.5.

Embodiment 17

The method of any one of the previous embodiments, wherein the aqueous composition hydrogel coating has a thickness of at least 0.1 mm.

Embodiment 18

The method of any one of the previous embodiments, wherein the aqueous composition hydrogel coating has a thickness of at least 2 mm.

Embodiment 19

The method of any one of the previous embodiments, wherein the aqueous composition further comprises an additive selected from at least one of polyethylene glycol, polyethylene glycol-co-polypropylene oxide copolymers, partially hydrolyzed polyvinyl acetate, polyvinyl pyrrolidone, glycerol or glycerol derivative, methylcellulose or other cellulose derivative, polyoxazoline, and natural gums.

Embodiment 20

The method of any one of the previous embodiments, wherein the aqueous composition further comprises an antimicrobial agent.

Embodiment 21

The method of any one of the previous embodiments, wherein the aqueous composition further comprises a crosslinking agent.

Embodiment 22

The method of embodiment 21, wherein the crosslinking agent is methylene bisacrylamide.

Embodiment 23

The method of any one of the previous embodiments, wherein the water-swellable clay is selected from at least one of laponite, synthetic hectorite, and montmorillonite.

Embodiment 24

The method of any one of the previous embodiments, wherein the acid is selected from the group consisting of citric acid, ascorbic acid, acetic acid, propanoic acid, lactic acid, succinic acid, tartaric acid, hydrochloric acid, sulfuric acid, benzoic acid, and mineral acid.

Embodiment 25

The method of any one of embodiments 1-23, wherein the salt is selected from the group consisting of an alkali metal salt, an alkaline earth metal salt, a chloride salt and an ammonium salt.

Embodiment 26

The method of any one of the previous embodiments, further comprising exposing the dried coated substrate to actinic radiation before applying the aqueous composition.

Embodiment 27

The method of any one of the previous embodiments, wherein the curing is by UV radiation.

Embodiment 28

A hydrogel article comprising:
(i) a polymeric substrate comprising an abstractable atom; and
(ii) a hydrogel coating thereon wherein the hydrogel coating has a water content of at least 10 wt % and is covalently bonded to the polymer substrate, and wherein the hydrogel coating is derived from an aqueous composition comprising:
(a) a hydrophilic monomer comprising a (meth)acrylamide, (meth)acrylate, and combinations thereof;
(b) at least 2 wt % of a water-swellable clay;
(c) a water-soluble type I photoinitiator; and
(d) an acid or salt,
wherein a water insoluble type II photoinitiator is localized at the interface between the hydrogel coating and the polymeric substrate.

Embodiment 29

The hydrogel article of embodiment 28, wherein the polymeric substrate comprises at least one of polyolefin, polyurethanes, polyamide, and polyester.

Embodiment 30

The hydrogel article of any one of embodiments 28-29, wherein the polymeric substrate is flexible.

Embodiment 31

The hydrogel article of any one of embodiments 28-30, wherein the water insoluble Type II photoinitiator comprises at least one of: benzophenone, xanthone, thioxanthone, Michler's ketone, benzyl, and anthraquinone.

Embodiment 32

The hydrogel article of any one of embodiments 28-31, wherein the aqueous solution comprises at least 20% solids.

Embodiment 33

The hydrogel article of any one of embodiments 28-32, wherein the hydrogel coating intimately contacts the polymeric substrate.

Embodiment 34

The hydrogel article of any one of embodiments 28-33, wherein the water soluble Type I photoinitiator is 2-hydroxy-4'-(2-hydroxyethoxy)-2-methyl propiophenone.

Embodiment 35

The hydrogel article of any one of embodiments 28-34, wherein the aqueous composition is substantially free of a C1-C5 alcohol.

Embodiment 36

The hydrogel article of any one of embodiments 28-35, wherein the aqueous composition is substantially free of a Type II initiator.

Embodiment 37

The hydrogel article of any one of embodiments 28-36, wherein the hydrogel coating has a pH of greater than 5 and less than 9.5.

Embodiment 38

The hydrogel article of any one of embodiments 28-37, wherein the hydrogel coating has a thickness of at least 0.1 mm.

Embodiment 39

The hydrogel article of any one of embodiments 28-38, wherein the aqueous composition further comprises an additive selected from at least one of polyethylene glycol, polyethylene glycol-co-polypropylene oxide copolymers, partially hydrolyzed polyvinyl acetate, polyvinyl pyrrolidone, glycerol or glycerol derivative, methylcellulose or other cellulose derivative, polyoxazoline, and natural gums.

Embodiment 40

The hydrogel article of any one of embodiments 28-39, wherein the aqueous composition further comprises an antimicrobial agent.

Embodiment 41

The hydrogel article of any one of embodiments 28-37, wherein the aqueous composition further comprises a crosslinking agent.

Embodiment 42

The hydrogel article of embodiment 41, wherein the crosslinking agent is methylene bisacrylamide.

Embodiment 43

The hydrogel article of any one of embodiments 28-42, wherein the water-swellable clay is selected from at least one of laponite, synthetic hectorite, and montmorillonite.

Embodiment 44

The hydrogel article of any one of embodiments 28-43, wherein the water insoluble Type II photoinitiator is within 50 nanometers from a first major surface of the polymeric substrate.

EXAMPLES

Unless otherwise noted, all parts, percentages, ratios, etc. in the examples and the rest of the specification are by weight, and all reagents used in the examples were obtained, or are available, from general chemical suppliers such as, for example, Sigma-Aldrich Company, Saint Louis, Mo., or may be synthesized by conventional methods.

These abbreviations are used herein: g=grams, mg=milligrams, mm=millimeters, cm=centimeters, nm=nanometers, mL=milliliters, L=liters, rpm=revolutions per minute, min=minutes, oC=degrees Celsius, wt=weight, and mW=milliWatt.

Materials:

| REAGENT | SOURCE |
| --- | --- |
| N,N-dimethylacrylamide (DMA) | Sigma-Aldrich Corporation, St. Louis, MO |
| Methylenebisacrylamide (MBA) | Sigma-Aldrich Corporation, St. Louis, MO |
| IRGACURE 2959 (1-[4-(2-hydroxyethoxy)phenyl]-2-hydroxy-2-methyl-1-propane-1-one) | BASF Corporation, Florham Park, NJ |
| LAPONITE XLG Clay | Southern Clay Products, Gonzales, TX |
| Citric acid | Alfa Aesar, Ward Hill, MA |
| Benzophenone | Alfa Aesar, Ward Hill, MA |
| Ammonium persulfate | Alfa Aesar, Ward Hill, MA |

Unless otherwise noted, all aqueous compositions were prepared with 18 MΩ water from a water purification system (available under the trade designation "Milli-Q" from EMD Millipore, Billerica, Mass.).

An Orion 3 Star pH Meter equipped with an 8157 BNC Ross Ultra pH/ATC Triode electrode (Thermo Scientific, Waltham, Mass.) was used to measure pH. The pH meter was calibrated using a three point calibration that followed the vendor provided procedure with calibration standards at pH 4, 7, and 10 (BDH, Dubai, UAE).

Aqueous Composition I

A glass jar (0.95 L) was equipped with an overhead stirrer (VOS PC Overhead Stirrer, available from VWR International, Radnor, Pa.) that had a 60 cm half-moon shaped impeller. The jar was charged with water (522 mL) and the overhead stirrer was set at 400 rpm. LAPONITE XLG clay (18 g) was slowly added and the mixture was stirred for 30 minutes. The resulting clear solution was charged with a solution that contained IRGACURE 2959 (300 mg) dissolved in N,N-dimethylacrylamide (62.4 mL). An aqueous solution of methylenebisacrylamide (3 mL, 2% by weight) was added next and the reaction was stirred for 30 minutes. An aqueous solution of ammonium persulfate (6 mL, 10% by weight) was then added and the reaction was stirred for 5 minutes. The mixing was stopped and the resulting aqueous composition was maintained for about 60 minutes in order to build the viscosity of the formulation. The pH of Aqueous Composition I was 9.1.

Example 2 and Comparative Example 2

A sheet (24.1 cm by 17.8 cm) of translucent polyurethane film (20 microns thick) with a white paper carrier backing (130 microns thick) on one side (available from the 3M Corporation, St. Paul, Minn. under the designation "3M 9832F Film on White Paper Carrier") was divided in two 12.05 cm by 8.9 cm sections using an imaginary line to define first and second sections. The polyurethane film surface of the first section was coated with 2 mL of a 1% by weight solution of benzophenone in hexane using a #14 Mayer rod. Any excess solution that accumulated at the edges of the coated section was carefully collected and removed using a paper towel. The coating was dried by the evaporation of solvent at ambient conditions. The polyurethane film surface of the second section was not coated with the benzophenone solution. The Aqueous Composition I from above (60 mL) was then applied to both sections of the polyurethane film using a notched bar applicator (2 mm gap setting) that also applied a clear PET release liner coated with a silicone release coating as a cover sheet (51 microns thick, obtained from Dupont Teijin Films, Dupont Company, Wilmington, Del.). The cover sheet was positioned so that the silicone release coating faced Aqueous Composition I. Ultraviolet (UV) light initiated grafting was conducted by irradiating the coated sheet for 20 minutes using a UV light stand (Classic Manufacturing, Inc., Oakdale, Minn.). The stand was equipped with sixteen 40 watt, 350 nm black light tubes [Sylvania RG2 F40/350BL/ECO tubes (117 cm long)] with 8 light tubes positioned in a row above the sheet and 8 tubes positioned in a row below the sheet. The light tubes in each row were spaced 5.1 cm on center and positioned 3.8 cm from the surface of the sheet. The first section of the sheet, which comprised the dried benzophenone coating) served as Example 2. The second section (that did not contain a dried benzophenone coating) served as a Comparative Example 2.

Example 3 and Comparative Example 3

The same procedure as reported in Example 2 and Comparative Example 2 was followed with the exception that the polyurethane film was coated with a 2% by weight solution of benzophenone in hexane, instead of a 1% by weight solution of benzophenone in hexane.

Example 4 and Comparative Example 4

The same procedure as reported in Example 2 and Comparative Example 2 was followed with the exception that the polyurethane film was coated with a 5% by weight solution of benzophenone in hexane, instead of a 1% by weight solution of benzophenone in hexane.

Example 5 and Comparative Example 5

The same procedure as reported in Example 2 and Comparative Example 2 was followed with the exception that the polyurethane film was coated with a 10% by weight solution of benzophenone in hexane, instead of a 1% by weight solution of benzophenone in hexane.

Example 6 and Comparative Example 6

The same procedure as reported in Example 2 and Comparative Example 2 was followed with the exception that the polyurethane film was coated with a 1% by weight solution of benzophenone in heptane, instead of a 1% by weight solution of benzophenone in hexane.

Example 7 and Comparative Example 7

The same procedure as reported in Example 2 and Comparative Example 2 was followed with the exception that the polyurethane film was coated with a 1% by weight solution of benzophenone in acetone, instead of a 1% by weight solution of benzophenone in hexane.

Example 8 and Comparative Example 8

The same procedure as reported in Example 5 and Comparative Example 5 was followed with the exception that the polyurethane film was replaced with a clear PET film (96.5 microns thick).
Aqueous Composition II
A glass jar (0.95 L) equipped with magnetic stir bar was charged with water (426 mL) and stirred at about 550 rpm. The LAPONITE XLG clay (15 g) was slowly added and the mixture was stirred for 30 minutes. The resulting clear solution was charged with N,N-dimethylacrylamide (50 mL) followed by an aqueous solution of methylenebisacrylamide (6.25 mL, 2% by weight) and stirred until the solution was clear. IRGACURE 2959 (250 mg) was added and the reaction was stirred for 10 minutes. A citric acid solution (1.9 mL, 10% by weight) was then added and the reaction was stirred for 5 minutes. The mixing was stopped and the resulting aqueous composition was maintained for 60 minutes in order to build the viscosity of the formulation. The pH of the Aqueous Composition II was 8.5.

Example 9

A sheet (30.5 cm by 61 cm) of translucent polyurethane film (20 microns thick) with a white paper carrier backing (130 microns thick) on one side (available from the 3M Corporation under the designation "3M 9832F Film on White Paper Carrier") was coated on the polyurethane film surface with 3 mL of a 1% by weight solution of benzophenone in hexane using a #14 Mayer rod. Any excess solution that accumulated at the edges of the coated section was carefully collected and removed using a paper towel. The coating was dried by the evaporation of solvent at ambient conditions. Aqueous Composition II was then applied to the polyurethane using a notched bar applicator (4 mm gap setting) that also applied a clear PET release liner coated with a silicone release coating as a cover sheet (51 microns thick, obtained from Dupont Teijin Films). The cover sheet was positioned so that the silicone release coating faced the hydrogel composition. Ultraviolet (UV) light initiated grafting was conducted by irradiating the coated sheet for 20 minutes using a UV light stand (Classic Manufacturing, Inc.). The stand was equipped with sixteen 40 watt, 350 nm black light tubes [Sylvania RG2 F40/350BL/ECO tubes (117 cm long)] with 8 light tubes positioned in a row above the sheet and 8 tubes positioned in a row below the sheet. The light tubes in each row were spaced 5.1 cm on center and positioned 3.8 cm from the surface of the sheet.

Example 10

The same procedure as reported in Example 9 was followed with the exception that Aqueous Composition II was applied to the polyurethane film using a notched bar applicator with a 6 mm gap setting, instead of a 4 mm gap setting.
Peel Test
Peel tests (T-Peel) were conducted on the hydrogel bonded polyurethane films of Examples 2-5 using a TA-XT Plus Texture Analyzer (Texture Technologies Corporation, Hamilton, Mass.). Test samples (5.1 cm long by 1.27 cm wide) were cut from each sheet so that the lengthwise direction contained about 2.55 cm from the first section and about 2.55 cm from the second section. The paper backing and PET cover sheet were both removed from the samples. For each sample the hydrogel of the first section was adhered to the polyurethane film, while the hydrogel of the second section was very poorly adhered to the polyurethane film such that the hydrogel coating could be readily separated by hand from the polyurethane film. Consequently, the polyurethane film and hydrogel from the second section were used as leads for attaching the first section to the instrument. The unattached hydrogel from the second section was secured in the lower grips of the instrument and the corresponding polyurethane film portion from the second section was secured in the upper grips of the instrument. The sample was then placed under tension at a separation rate of 50 mm/minute. This configuration allowed for a determination of the peel adhesion for the first section of the samples. The measured force (g) and travel distance (mm) for each example was recorded with Exponent Software (Stable MicroSystems, Ltd., Hamilton, Mass.). The same peel test was also conducted using a 5.1 cm long by 1.27 cm wide sample taken entirely from the second section of Example 2 (i.e., Comparative Example 2). The results are presented in Table 1.

TABLE 1

| | Weight % of Benzophenone in the Coating Solution | Force (g) Measured at Specified Travel Distance (mm) | | | | |
|---|---|---|---|---|---|---|
| | | 5 mm | 10 mm | 20 mm | 30 mm | 40 mm |
| Comparative Example 2 | 0% | 15 g | 0.5 g | 0.4 g | 2.0 g | 0 g |
| Example 2 | 1% | 4.5 g | 15.1 g | 21.0 g | 28.5 g | 33.1 g |
| Example 3 | 2% | 8.1 g | 24.9 g | 56.8 g | 85.5 g | 113.6 g |
| Example 4 | 5% | 3.3 g | 15.2 g | 43.2 g | 69.4 g | 93.3 g |
| Example 5 | 10% | 10.4 g | 23.2 g | 46.3 g | 68.8 g | 96.6 g |

Foreseeable modifications and alterations of this invention will be apparent to those skilled in the art without departing from the scope and spirit of this invention. This invention should not be restricted to the embodiments that are set forth in this application for illustrative purposes.

What is claimed is:

1. A method of making a grafted hydrogel comprising the steps in the order of:
   (a) obtaining a polymeric substrate having an abstractable atom;
   (b) coating the polymeric substrate with a Type II photoinitiator to form a dried coated substrate;
   (c) applying an aqueous composition to form an aqueous coated substrate, wherein the aqueous composition, wherein the aqueous composition comprises (i) a hydrophilic monomer comprising a (meth)acrylamide, (meth)acrylate, and combinations thereof; (ii) 2-20% wt water-swellable clay, and (iii) a water soluble Type I photoinitiator, and (iv) a salt or acid;
   (d) curing the aqueous coated substrate.

2. The method of claim 1, wherein the polymeric substrate comprises at least one of polyolefin, polyurethanes, polyamide, and polyester.

3. The method of claim 1, wherein the polymeric substrate is flexible.

4. The method of claim 1, wherein the polymeric substrate is coated with a water insoluble Type II photoinitiator.

5. The method of claim 1, wherein step (b) is performed by coating a liquid comprising the Type II photoinitiator and a solvent onto the polymeric substrate followed by removing the solvent to form the dried coated substrate.

6. The method of claim 5, wherein the liquid comprises at least 0.1 wt % of water insoluble Type II photoinitiator.

7. The method of claim 1, wherein the aqueous solution comprises at least 20% solids.

8. The method of claim 1, wherein the aqueous composition intimately contacts the dried coated substrate.

9. The method of claim 1, wherein the aqueous composition comprises 0.001 to 5% by weight of the water soluble Type I photoinitiator.

10. The method of claim 1, wherein the aqueous composition is substantially free of a C1-C5 alcohol.

11. The method of claim 1, wherein the aqueous composition has a pH of greater than 5 and less than 9.5.

12. The method of claim 1, wherein the aqueous composition hydrogel coating has a thickness of at least 0.1 mm.

13. The method of claim 1, wherein the aqueous composition hydrogel coating has a thickness of at least 2 mm.

14. A hydrogel article comprising:
   a polymeric substrate comprising an abstractable atom; and
   (ii) a hydrogel coating thereon wherein the hydrogel coating has a water content of at least 10 wt % and is covalently bonded to the polymer substrate, and wherein the hydrogel coating is derived from an aqueous composition comprising:
   (a) a hydrophilic monomer comprising a (meth)acrylamide, (meth)acrylate, and combinations thereof;
   (b) at least 2 wt % of a water-swellable clay;
   (c) a water-soluble type I photoinitiator; and
   (d) an acid or salt,
   wherein a water insoluble type II photoinitiator is localized at the interface between the hydrogel coating and the polymeric substrate.

15. The hydrogel article of claim 14, wherein the water insoluble Type II photoinitiator is within 50 nanometers from a first major surface of the polymeric substrate.

16. The method of claim 1, wherein the aqueous composition is substantially free of a Type II initiator.

17. The method of claim 1, wherein the aqueous composition further comprises an additive selected from at least one of polyethylene glycol, polyethylene glycol-co-polypropylene oxide copolymers, partially hydrolyzed polyvinyl acetate, polyvinyl pyrrolidone, glycerol or glycerol derivative, methylcellulose or other cellulose derivative, polyoxazoline, and natural gums.

18. The method of claim 1, wherein the aqueous composition further comprises a crosslinking agent.

19. The method of claim 1, wherein the acid is selected from the group consisting of citric acid, ascorbic acid, acetic acid, propanoic acid, lactic acid, succinic acid, tartaric acid, hydrochloric acid, sulfuric acid, benzoic acid, and mineral acid.

20. The method of claim 5, wherein the liquid consists essentially of the Type II photoinitiator and the solvent.

* * * * *

UNITED STATES PATENT AND TRADEMARK OFFICE
CERTIFICATE OF CORRECTION

PATENT NO. : 11,278,639 B2
APPLICATION NO. : 16/485580
DATED : March 22, 2022
INVENTOR(S) : Alexi J Young et al.

It is certified that error appears in the above-identified patent and that said Letters Patent is hereby corrected as shown below:

In the Claims

Column 21
Line 54-55, In Claim 1, delete "wherein the aqueous composition, wherein the aqueous composition" and insert -- wherein the aqueous composition --, therefor.

Signed and Sealed this
Fifteenth Day of November, 2022

Katherine Kelly Vidal
*Director of the United States Patent and Trademark Office*